(12) United States Patent
Arba-Mosquera et al.

(10) Patent No.: US 11,590,026 B2
(45) Date of Patent: Feb. 28, 2023

(54) METHOD FOR CONTROLLING AN EYE SURGICAL LASER AND TREATMENT DEVICE

(71) Applicant: SCHWIND EYE-TECH-SOLUTIONS GMBH, Kleinostheim (DE)

(72) Inventors: Samuel Arba-Mosquera, Aschaffenburg (DE); Shwetabh Verma, Aschaffenburg (DE); Nico Triefenbach, Mainaschaff (DE); Mario Shraiki, Stockstadt (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 0 days.

(21) Appl. No.: 16/823,571

(22) Filed: Mar. 19, 2020

(65) Prior Publication Data
US 2020/0297537 A1 Sep. 24, 2020

(30) Foreign Application Priority Data
Mar. 20, 2019 (DE) ...................... 10 2019 107 182.8

(51) Int. Cl.
*A61F 9/008* (2006.01)
*A61B 17/00* (2006.01)
(Continued)

(52) U.S. Cl.
CPC ...... *A61F 9/00827* (2013.01); *A61F 9/00804* (2013.01); *A61F 9/00814* (2013.01);
(Continued)

(58) Field of Classification Search
CPC .............. A61F 9/00827; A61F 9/00804; A61F 9/00836; A61F 9/00814; A61F 9/00838;
(Continued)

(56) References Cited

U.S. PATENT DOCUMENTS

| 2006/0020259 A1* | 1/2006 | Baumeister | ............. A61F 9/009 606/107 |
| 2010/0087802 A1* | 4/2010 | Bischoff | ............. A61F 9/00831 606/4 |

(Continued)

FOREIGN PATENT DOCUMENTS

DE 103 34 108 A1 2/2005

*Primary Examiner* — Mallika D Fairchild
*Assistant Examiner* — Shreya Anjaria
(74) *Attorney, Agent, or Firm* — Medler Ferro Woodhouse & Mills PLLC

(57) ABSTRACT

A method of controlling an eye surgical laser is disclosed for the separation of a volume body with predefined posterior and anterior interfaces from a human/animal cornea. The method including controlling the laser with a control device, the laser being configured to emit pulsed laser pulses in a predefined pattern into the cornea. The posterior and anterior interfaces of the volume body are defined by the predefined pattern and are generated by an interaction of the individual laser pulses with the cornea through photodisruption. The control device controls the laser beam such that both interfaces are generated via a continuous, uninterrupted sequence of laser pulses. A treatment device is disclosed with at least one eye surgical laser for the separation of a predefined corneal volume with predefined interfaces of a human/animal eye by photodisruption and with at least one control device for the laser(s).

16 Claims, 2 Drawing Sheets

(51) Int. Cl.
*A61B 18/00* (2006.01)
*A61B 18/20* (2006.01)
*A61D 1/00* (2006.01)

(52) U.S. Cl.
CPC .............. *A61F 9/00836* (2013.01); *A61B 2017/00172* (2013.01); *A61B 2018/00601* (2013.01); *A61B 2018/20355* (2017.05); *A61D 1/00* (2013.01); *A61F 2009/00872* (2013.01); *A61F 2009/00882* (2013.01)

(58) Field of Classification Search
CPC . A61F 2009/00882; A61F 2009/00872; A61B 2017/00172; A61B 2018/00601; A61B 2018/20355; A61B 18/203; A61D 1/00
See application file for complete search history.

(56) References Cited

U.S. PATENT DOCUMENTS

2013/0281992 A1* 10/2013 Seiler ................. A61F 9/00827
606/5
2015/0366711 A1* 12/2015 Bischoff ............. A61F 9/00827
606/5

* cited by examiner

METHOD FOR CONTROLLING AN EYE SURGICAL LASER AND TREATMENT DEVICE

FIELD

The present invention relates to methods for controlling an eye surgical laser for the separation of a volume body with a predefined posterior interface and a predefined anterior interface from a human or animal cornea. Furthermore, the invention relates to a treatment device with at least one eye surgical laser for the separation of a predefined corneal volume with predefined interfaces of a human or animal eye by means of photodisruption and with at least one control device for the laser or lasers as well as to a computer program and a computer-readable medium.

BACKGROUND

Devices and methods for controlling a photoablative ophthalmologic laser are known. Thus, EP 1 628 606 B1 describes a method and a device for precisely processing organic tissue by means of a laser, wherein a pulsed laser and a beam focusing device are formed such that the laser beam pulses effect a photodisruption in a focus located within the organic material. However, it is disadvantageous in these known methods and devices that the posterior and anterior interfaces of the volume body to be separated are always separated and generated temporally offset and temporally interrupted, respectively, in the known photodisruptive methods and devices. In particular, the posterior interface farther spaced from the corneal surface is first swept with the laser beam. After completing the posterior interface, the laser is turned off and a displacement, in particular horizontal displacement of the laser focus towards the anterior interface still to be produced, is effected. After reaching and adjusting the laser focus to the anterior interface, the laser is again put into operation and the anterior interface is swept with the newly focused laser beam. However, such a method results in treatment times taking relatively long, which can adversely affect the patient.

BRIEF SUMMARY

Therefore, it is the object of the present invention to provide a method and a treatment device for controlling an eye surgical laser for the separation of a volume body with predefined interfaces from a human or animal cornea, by which the disadvantages of the prior art are overcome.

A generic method according to the features of claim 1, a generic treatment device with the features of claim 14 as well as a computer program according to the features of claim 17 and a computer-readable medium according to the features of claim 18 serve for solving this object.

Advantageous configurations with convenient developments of the invention are specified in the respective dependent claims, wherein advantageous configurations of the method are to be regarded as advantageous configurations of the treatment device, of the computer program and of the computer-readable medium and vice versa.

A first aspect of the invention relates to a method for controlling an eye surgical laser for the separation of a volume body with a predefined posterior interface and a predefined anterior interface from a human or animal cornea, comprising controlling the laser by means of a control device such that the laser emits pulsed laser pulses in a predefined pattern into the cornea, wherein the interfaces of the volume body to be separated are defined by the predefined pattern and the interfaces are generated by means of an interaction of the individual laser pulses with the cornea by means of photodisruption. Therein, the control device controls the laser beam such that both interfaces are generated by means of a continuous, uninterrupted sequence of the laser pulses. By the method according to the invention, it is possible to generate the posterior and anterior interfaces of the volume body to be separated in one method step. Thereby, the treatment duration can be considerably shortened since turning off the laser and new focusing of the laser beam are not required.

Therein, the control device can control the laser beam such that the posterior interface is generated in a first step by means of an incision course of the laser beam starting from a central area of the eye and ending in a predetermined edge area of the cornea. In addition, the control device can control the laser beam such that the anterior interface is generated in a second step by means of an incision course of the laser beam starting from the predetermined edge area of the cornea and ending in a central area of the eye, wherein the laser beam executes a change of the direction of movement in a transition zone between the first and the second interface in the edge area of the cornea. By the change of the direction of movement of the laser or laser beam, it is advantageously possible to generate the interfaces of the volume body to be separated in "one incision". Thus, the treatment duration is considerably shortened. In addition, it is ensured that a connection between the posterior and the anterior interface is always formed such that the removal of the volume body is possible without problems. Possible "tissue bridges" between the interfaces are reliably prevented.

Therein, the laser can be controlled such that at least one incision or at least one opening is generated in the cornea at a predefined angle and with a predefined geometry, wherein the incision or the opening intersects an interface of the volume body and is formed up to a surface of the cornea such that the volume body is removable from the cornea via the incision or the opening. Therein, the volume body can be lenticularly formed, whereby simple removal via the mentioned incision or the mentioned opening is possible. In that the volume body to be separated is only described and defined by the interfaces and they are generated by means of photodisruption on the other hand, a full-area and full-volume ablation of the volume body, respectively, can be omitted. Only the interfaces are generated by means of photodisruption such that the predefined volume body can subsequently be removed from the cornea.

In further advantageous configurations of the method according to the invention, the laser is controlled such that the predefined pattern is at least partially circularly and/or spirally ablated. Therein, the start of the photodisruption by the individual laser pulses can be effected in the center of the respective interface or also at the edge of the respective interface. Thus, the laser beam can be controlled such that the individual laser pulses are guided in a spiral leading from the inside to the outside in the posterior interface and the individual laser pulses are guided starting from the transition zone in a spiral leading from the outside to the inside in the anterior interface. Such an incision course and guiding of the laser beam, respectively, can be fast and precisely performed.

In further advantageous configurations of the method according to the invention, the predefined pattern is defined based on one or more control datasets, wherein the control dataset or datasets include control data for positioning and/or for focusing individual laser pulses in the cornea. The determination of the control datasets is known and in particular results from the topographic and/or pachymetric measurement of the cornea to be treated as well as the type of the visual disorder to be corrected. In particular, the control datasets are generated at least by providing topographic and/or pachymetric and/or morphologic data of the untreated cornea and providing topographic and/or pachymetric and/or morphologic data of the volume body to be removed within the cornea. Therein, the volume body to be separated is formed such that a refractive correction of the eye is additionally effected by the removal of the volume body. The mentioned visual disorders of the eye can be myopia, hyperopia, presbyopia, astigmatism or also other visual disorders of the eye.

Furthermore, there is the possibility that the pathologically changed area within the cornea is an opacification and/or a scar.

In further advantageous configurations of the method according to the invention, at least the posterior interface is formed at least partially straight and/or curved and/or wave-like and/or serrated and/or smooth. Other topographic configurations of the posterior interface are also conceivable.

In further advantageous configurations of the method according to the invention, the control device is formed such that the laser emits laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz. Such lasers are already used for photodisruptive methods in the eye surgery. Thus, EP 2 211 803 B1 for example describes a corresponding femto-second laser, which is used for producing a so-called lenticule, that is a lenticular volume body, within the cornea. The lenticule thus produced is subsequently removed from the cornea via an incision in it. The use of photodisruptive lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that high incision accuracy in the generation of the interfaces is ensured.

In further advantageous configurations of the method according to the invention, the surface of the cornea is a natural surface of the eye or a surface of the eye artificially generated by means of ablation or displacement of an uppermost corneal layer and/or by means of production of a corneal flap. Thereby, the method according to the invention is usable for a plurality of phototherapeutic methods.

A second aspect of the present invention relates to a treatment device with at least one eye surgical laser for the separation of a predefined corneal volume with predefined interfaces of a human or animal eye by means of photodisruption and at least one control device for the laser or lasers, which is formed for executing the steps of the method according to the first aspect of the invention. The treatment device according to the invention allows that the disadvantages, in particular relatively long treatment times, occurring in using usual ablative treatment devices are reliably avoided.

Therein, the laser is suitable to emit laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz.

In further advantageous configurations of the treatment device according to the invention, the control device comprises at least one storage device for at least temporary storage of at least one control dataset, wherein the control dataset or datasets include control data for positioning and/or for focusing individual laser pulses in the cornea; and at least one beam device for beam guidance and/or beam shaping and/or beam deflection and/or beam focusing of a laser beam of the laser. Therein, the mentioned control datasets are usually generated based on a measured topography and/or pachymetry and/or morphology of the cornea to be treated and the type of the visual disorder to be corrected.

Further features and the advantages thereof can be taken from the description of the first inventive aspect, wherein advantageous configurations of each inventive aspect are to be regarded as advantageous configurations of the respectively other inventive aspect.

A third aspect of the invention relates to a computer program including instructions, which cause the treatment device according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and the second inventive aspect, wherein advantageous configurations of each inventive aspect are to be regarded as advantageous configurations of the respectively other inventive aspect.

BRIEF DESCRIPTION OF THE FIGURES

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims. There shows FIG. 1 a schematic representation of a treatment device according to the invention.

DETAILED DESCRIPTION

Figure 1:
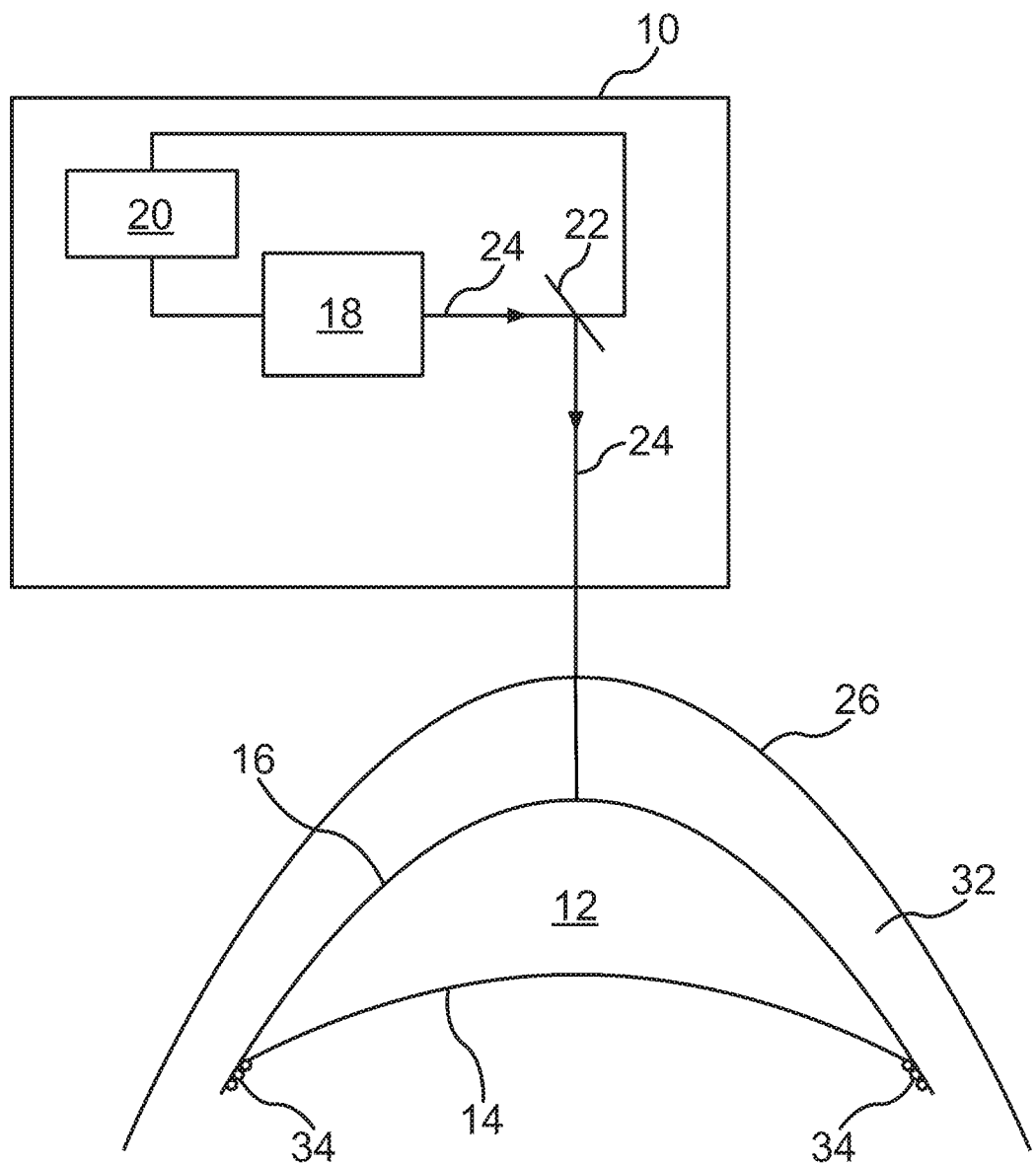

FIG. 1 shows a schematic representation of a treatment device 10 with an eye surgical laser 18 for the separation of a predefined corneal volume or volume body 12 with each a predefined posterior and anterior interface 14, 16 of a cornea 32 of a human or animal eye by means of photodisruption. One recognizes that a control device 20 for the laser 18 is formed besides the laser 18 such that the laser 18 emits pulsed laser pulses in a predefined pattern into the cornea, wherein the interfaces 14, 16 of the volume body 12 to be separated are generated by means of photodisruption by the predefined pattern. In the illustrated embodiment, the interfaces 14, 16 form a lenticular volume body 12, wherein the configuration and position of the volume body 12 are selected such that a desired refractive alteration for removal of a visual disorder occurs after removing the volume body 12 from the cornea 32. Furthermore, it is apparent from FIG. 1 that the laser beam 24 generated by the laser 18 is deflected by means of a beam device 22, namely a beam deflecting device, such as for example a scanner, in the direction of a surface 26 of the cornea. In the illustrated embodiment, the surface 26 is shaped by abutting the eye on an abutment plate, transparent, i.e. light-transmissive, at least in central areas, of a so-called patient interface (not illustrated). With the aid of the patient interface, the coupling of the eye to the laser 18 and to the treatment device 10, respectively, is effected. The beam deflecting device 22 is also controlled by the control device 20 to generate the mentioned predefined pattern in the cornea 32. Furthermore, one recognizes that a transition zone 34 is formed, which connects the interfaces 14, 16 to each other, such that tissue bridges cannot arise in this intermediate area, which aggravate or even prevent a possible separation of the volume body 12 from the cornea 32.

The illustrated laser 18 is a photodisruptive laser, which is formed to emit laser pulses in a wavelength range between 300 nm and 1400 nm, preferably between 900 nm and 1200 nm, at a respective pulse duration between 1 fs and 1 ns, preferably between 10 fs and 10 ps, and with a repetition frequency of greater than 10 KHz, preferably between 100 KHz and 100 MHz.

The control device 20 additionally comprises a storage device (not illustrated) for at least temporary storage of at least one control dataset, wherein the control dataset or datasets include control data for positioning and/or for focusing individual laser pulses in the cornea. The position data and/or focusing data of the individual laser pulses are generated based on a previously measured topography and/or pachymetry and/or the morphology of the cornea 32 and the desired refractive correction.

Figure 2:
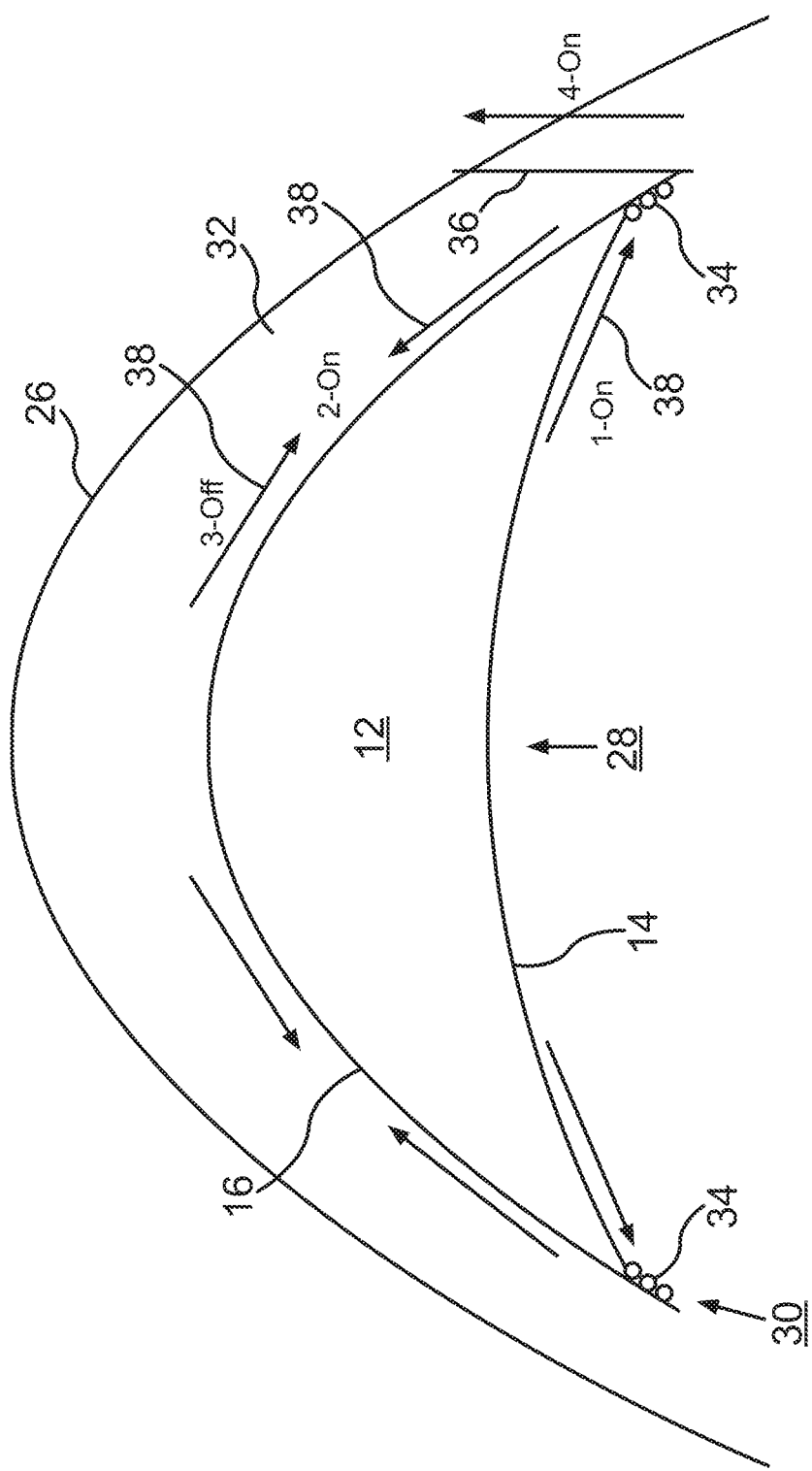
FIG. 2 a schematic diagram of the generation of a volume body to be separated according to the method according to the invention.

FIG. 2 shows a schematic diagram of the generation of the volume body 12 to be separated according to an embodiment of the present method. One recognizes that the interfaces 14, 16 are generated by means of the pulsed laser beam 24, which is directed towards the cornea or towards the surface 26 of the cornea via the beam deflecting device 22. Therein, the posterior and the anterior interface 14, 16 overall form a lenticular volume body 12. Furthermore, the laser 18 generates a further incision 36 in the illustrated embodiment, which intersects the volume body 12 at a predefined angle and with a predefined geometry and is formed up to the surface 26 of the cornea. The volume body 12 defined by the interfaces 14, 16 can then be removed from the cornea 32 via the incision 34.

In the illustrated embodiment, it is apparent that the interfaces 14, 16 are generated by means of an interaction of the individual laser pulses with the cornea 32 by means of photodisruption. Therein, the laser beam 24 is controlled such that both interfaces 14, 16 are generated by means of a continuous, uninterrupted sequence of the laser pulses.

This is to be clarified by the movement arrows 38, which are to schematically represent the guidance of the laser beam 24 along the interfaces 14, 16. In the illustrated embodiment, the laser beam 24 is controlled by the control device 20 (compare FIG. 1) such that the posterior interface 14 is generated in a first step by means of an incision course of the laser beam 24 starting from a central area 28 of the eye and ending in a predetermined edge area 30 of the cornea 32. Starting from the central area 28, the laser beam is therein spirally guided towards the edge areas 30 up to the transition zone 34, that is from the inside to the outside. This is to be schematically represented by the corresponding direction arrows 38. Furthermore, it is illustrated by the designation "1-ON" that the laser 18 (compare FIG. 1) is activated and generates the laser beam 24.

Furthermore, one recognizes that the laser beam 24 is controlled such that the anterior interface 16 is generated in a second step by means of an incision course of the laser beam 24 starting from the predetermined edge area 30 in the transition zone 34 of the cornea 32 and ending in the central area 28 of the eye. Therein, the laser beam 24 executes a change of the direction of movement in the transition zone 34 between the first and the second interface 14, 16 in the edge area 30 of the cornea 32. This is again illustrated by corresponding movement arrows 38, wherein it is additionally illustrated by the reference character "2-ON" that the laser 18 is further in operation and generates the previously mentioned continuous, uninterrupted sequence of the laser pulses for generating the two interfaces 14, 16. The laser beam 24 is again spirally guided, wherein the interface 16 is generated by a spiral guidance from the outside, that is the edge area 30, to the inside, that is the central area 28 of the eye. After completion of the anterior interface 16, turning off the laser 18 (see reference character "3-OFF") and new focusing of the laser beam 18 in the edge area 30 of the cornea 32 are then effected. After completion of this new focusing, an incision 36 is generated in the cornea by means of the laser beam 24, wherein the incision 36 intersects an interface 14, 16 of the volume body 12 and is formed up to the surface 26 of the cornea such that the volume body 12 is removable from the cornea 32 via the incision 36. The new activation of the laser 18 and the direction of movement of the laser beam 24 are illustrated by the direction arrow "4-ON". Furthermore, it becomes clear that the interfaces 14, 16 are always in connection with each other by the formation of the transition zone 34, that is tissue bridges do not arise, which can aggravate or even prevent a possible separation of the volume body 12 from the cornea 32.

What is claimed is:

1. A method for controlling an eye surgical laser for the separation of a volume body with a predefined posterior interface and a predefined anterior interface from a human or animal cornea, comprising:

controlling the eye surgical laser by means of a control device such that the eye surgical laser emits pulsed laser pulses in a predefined pattern into the human or animal cornea, wherein the interfaces of the volume body to be separated are defined by the predefined pattern and the interfaces are generated by means of an interaction of the individual pulsed laser pulses with the human or animal cornea by means of photodisruption, wherein the control device controls a laser beam of the eye surgical laser such that both interfaces are generated by means of a continuous, uninterrupted sequence of the pulsed laser pulses along the interfaces, wherein the control device controls the laser beam such that the posterior interface is generated in a first step by means of an incision course of the laser beam starting from a central area of an eye and ending in a predetermined edge area of the human or animal cornea, wherein the control device controls the laser beam such that the anterior interface is generated in a second step by means of an incision course of the laser beam starting from the predetermined edge area of the human or animal cornea and ending in the central area of the eye, wherein the laser beam executes a change of a direction of movement in a transition zone between the posterior interface and the anterior interface in the predetermined edge area of the human or animal cornea, and wherein the control device controls the laser beam to generate the interfaces of the volume body to be separated in one incision.

2. The method according to claim 1, wherein the volume body is lenticularly formed.

3. The method according to claim 1, wherein the eye surgical laser is controlled such that at least one incision or at least one opening is generated in the human or animal cornea at a predefined angle and with a predefined geometry, wherein the at least one incision or the at least one opening intersects at least one of the posterior and anterior interfaces of the volume body and is formed up to a surface of the human or animal cornea such that the volume body is removable from the human or animal cornea via the incision or the opening.

4. The method according to claim 1, wherein the laser beam is controlled such that it is at least partially circularly and/or spirally guided along or over the predefined pattern.

5. The method according to claim 1, wherein the laser beam is controlled such that the individual pulsed laser pulses are guided in a spiral leading from the inside to the outside in the posterior interface and the individual pulsed laser pulses are guided in a spiral leading from the outside to the inside starting from the transition zone between the posterior interface and the anterior interface.

6. The method according to claim 1, wherein the predefined pattern is defined based on one or more control datasets, wherein the one or more control datasets include control data for positioning and/or for focusing individual pulsed laser pulses in the human or animal cornea.

7. The method according to claim 6, wherein the one or more control datasets are generated at least by providing topographic and/or pachymetric and/or morphologic data of the untreated human or animal cornea.

8. The method according to claim 1, wherein the volume body to be separated is furthermore formed such that a correction of a visual disorder of the eye is additionally effected by the removal of the volume body.

9. The method according to claim 1, wherein at least the posterior interface is formed at least partially straight and/or curved and/or wave-like and/or serrated and/or smooth.

10. The method according to claim 1, wherein the control device is configured such that the eye surgical laser emits pulsed laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz.

11. The method according to claim 3, wherein the surface of the human or animal cornea is a natural surface of the eye or a surface of the eye artificially generated by means of ablation or displacement of an uppermost corneal layer and/or by means of production of a corneal flap.

12. A treatment device with at least one eye surgical laser for the separation of a corneal volume with predefined interfaces of a human or animal eye by means of photodisruption and with at least one control device for the at least one eye surgical laser or lasers, which is configured to execute the steps of the method according to claim 1.

13. The treatment device according to claim 12, wherein the at least one eye surgical laser is suitable to emit pulsed laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz.

14. The treatment device according to claim 12, wherein the control device comprises at least one storage device for the at least temporary storage of at least one control dataset, wherein the control dataset or datasets include control data for positioning and/or for focusing individual pulsed laser pulses in the human or animal cornea; and comprises at least one beam device for beam guidance and/or beam shaping and/or beam deflection and/or beam focusing of a laser beam of the at least one eye surgical laser.

15. A computer program including instructions, which cause a treatment device with at least one eye surgical laser for the separation of a corneal volume with predefined interfaces from a human or animal eye by means of photodisruption and with at least one control device for the at least one eye surgical laser or lasers to execute the method steps according to claim 1.

16. A computer-readable medium, on which the computer program according to claim 15 is stored.

* * * * *